US00PP14065P39

(12) United States Plant Patent
Moser

(10) Patent No.: US PP14,065 P3
(45) Date of Patent: Aug. 19, 2003

(54) CHRYSANTHEMUM PLANT NAMED 'MOZA CB 01'

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 21 days.

(21) Appl. No.: 09/865,151

(22) Filed: May 24, 2001

(65) Prior Publication Data

US 2002/0178477 P1 Nov. 28, 2002

(51) Int. Cl.[7] ..... A01H 5/00

(52) U.S. Cl. ..... Plt./296

(58) Field of Search ..... Plt./296

*Primary Examiner*—Bruce R. Campell
*Assistant Examiner*—Anne Marie Grünberg
(74) *Attorney, Agent, or Firm*—Knobbe, Martens, Olson & Bear, LLP

(57) ABSTRACT

A new and distinct Chrysanthemum plant variety characterized by a daisy type inflorescence with many tightly held ray florets, consistent flowering response to short days, blooming consistently after 49 days of short day length, compact growth habit, and consistent natural season flowering habit during mid September.

1 Drawing Sheet

LATIN NAME OF THE GENUS AND SPECIES OF THE PLANT CLAIMED
*Chrysanthemum morifolium.*
VARIETY DENOMINATION
'MOZA CB 01'.

BACKGROUND OF THE INVENTION

The present invention relates to a new and distinct cultivar of Chrysanthemum plant, herein after referred to by the cultivar name 'MOZA CB 01.'

This new cultivar originated from hybridization of a female parent Chrysanthemum cultivar MZ 282-01 (unpatented in the United States) and a male parent Chrysanthemum cultivar MZ 365-01 (unpatented in the United States). The new cultivar was discovered by the inventor in November 1998.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'MOZA CB 01' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'MOZA CB 01.' These characteristics in combination distinguish 'MOZA CB 01' as a new and distinct Chrysanthemum:

1. Daisy type inflorescence with many tightly held ray florets;
2. Consistent flowering response to short days, blooming consistently after 49 days of short day length;
3. Compact growth habit; and
4. Consistent natural season flowering habit during mid September.

Plants of the new cultivar are similar to plants of the female parent cultivar in most horticultural characteristics, however plants of the new cultivar differed from plants of the female parent cultivar in the following characteristics:

1. The new cultivar has different color ray florets;
2. The new cultivar is taller;
3. The new cultivar has a different type bloom; and
4. The new cultivar has shorter internode length.

Plants of the new cultivar are similar to plants of the male parent cultivar in most horticultural characteristics, however plants of the new cultivar differed from plants of the male parent cultivar in the following characteristics:

1. The new cultivar has a smaller diameter bloom;
2. The new cultivar is shorter; and
3. The new cultivar has different color ray florets.

BRIEF DESCRIPTION OF THE PHOTOGRAPHS

The photograph shows a plant of the new cultivar grown in a 4-inch container. A single cutting was propagated in the container. It was planted in mid-July and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants that were approximately 85 days old, which were grown in a commercial field on Oxnard, Calif. in the month of September 2000. The plants were grown from a rooted cutting given one pinch after 10 days from planting. There was no spray or disbud treatment given. The growing conditions range from 60° to 65° F. at night to 70° to 85° during the day. Measurements and numerical values represent averages of typical flowering types.

Botanical classification: *Chrysanthemum morifolium* cultivar 'MOZA CB 01'.
Commercial classification: Garden-type Chrysanthemum.

Parentage: Hybridization of female parent Chrysanthemum cultivar MZ 282-01 (unpatented in the United States, and undistributed commercially) with a male parent Chrysanthemum cultivar MZ 365-01 (unpatented in the United States, and undistributed commercially)

Comparison variety: "Roadrunner" U.S. Plant Pat. No. 11,298, the most similar multi-color ray floret variety.

The new variety differs from Roadrunner in having a later natural season bloom time, smaller diameter inflorescence, pink/white ray florets as opposed to red/yellow ray florets, more ray florets and more disc florets than Roadrunner.

PROPAGATION

Time to rooting: 7 to 14 days at approximately 21° C.
Rooting habit: Fine, fibrous.

PLANT

Growth habit: Mounding herbaceous perennial.
Height: Approximately 25 cm.
Internode length: Approximately 2.1 cm.
Branching characteristics: Free Branching.
Length of lateral branches: Approximately 21 cm.
Number of leaves per lateral branch: Approximately 19.
Stem color: Near 137A.

FOLIAGE

Leaf:
- *Arrangement.*—Alternate single.
- *Average length.*—Approximately 4.0 cm.
- *Average width.*—Approximately 2.9 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Color.*—Young foliage upper side: Near 147A. Young foliage under side. Near 147B. Mature foliage upper side: Near 147A. Mature foliage under side: Near 147B. Venation upper side: Near 148A. Venation under side: Near 148B.

Petiole:
- *Average length.*—Approximately 1.3 cm.
- *Petiole color.*—Approximately 137B.

BLOOM

Inflorescence:
- *Flowering habit.*—Induced by darkness period greater than 13.5 hours, blooming consistently after 49 days of appropriate day length required to induce and develop blooms.
- *Inflorescence form.*—Daisy.
- *Natural flowering season.*—Approximately mid-September.
- *Number of inflorescences per stem.*—Approximately 20 to 30.
- *Inflorescence diameter.*—Approximately 2.5 cm.
- *Inflorescence depth.*—Approximately 0.8 cm.
- *Disc diameter.*—Approximately 0.1 cm.
- *Inflorescence longevity on plant.*—Approximately 25–30 days.
- *Persistence.*—Persistent.
- *Fragrance.*—Not present.

Ray florets:
- *Appearance.*—Matte.
- *Texture.*—Smooth.
- *Average number per flower.*—Approximately 70 to 80.
- *Shape.*—Cylindric.
- *Margin.*—Entire.
- *Apex.*—Obtuse.
- *Length.*—Approximately 1.0 cm.
- *Width.*—Approximately 0.4 cm.
- *Color.*—Upper surface at first opening: on 25% nearest base: Near 12A. Upper surface at first opening: on 75% nearest apex: Near 173A. Upper surface at maturity: on 50% nearest base: Near 12A. Upper surface at maturity: on 50% nearest apex: Near 173A. Upper surface at fading: on 50% nearest base: Near 12A. Upper surface at fading: on 50% nearest apex: Near 173A. Under surface at first opening: Near 9B, with a hint of 35A. Under surface at maturity: Near 9B, with a hint of 35A. Under surface at fading: Near 9B, with a hint of 35A.

Disc florets:
- *Appearance.*—Shiny.
- *Texture.*—Smooth.
- *Average number per flower.*—Approximately 120 to 130.
- *Shape.*—Cylindric.
- *Apex.*—Obtuse.
- *Average length.*—Approximately 0.4 cm.
- *Average width .*—Approximately 0.1 cm..
- *Color.*—At first opening. Near 15A. At maturity: Near 15A. At fading: Near 15A.

Peduncle:
- *Length.*—At terminal end (shortest): Approximately 3 cm. At lateral end (longest): Approximately 4.6 cm
- *Strength.*—Moderate.
- *Color.*—Near 146B.
- *Habit.*—Erect.

Inflorescence bud:
- *Length.*—Approximately 0.6 cm.
- *Diameter.*—Approximately 0.7 cm.
- *Form.*—Globular.
- *Color.*—50% of bud near 147B, 50% of bud near 154A.

Sepals:
- *Appearance.*—Matte.
- *Texture.*—Lightly pubescent.
- *Number.*—Approximately 20 to 30.
- *Shape.*—Ovate.
- *Margin.*—Entire.
- *Apex.*—*Acute.*
- *Color.*—Upper side: Near 137B. Under side: Near 137B.

REPRODUCTIVE ORGANS

Ray florets:
- *Number of pistils per floret.*—1.
- *Stigma shape.*—2 branched.
- *Stigma color.*—Near 15A.
- *Stigma length.*—Approximately 0.1 cm.
- *Style color.*—Near 7A.
- *Style length.*—Approximately 0.3 cm.
- *Number of stemens per floret.*—Absent.

Disc florets:
- *Number of pistils per floret.*—1.
- *Stigma shape.*—Cylindric.
- *Stigma color.*—Approximately 1A.
- *Style color.*—Approximately 1C.

*Number of stamens per floret.*—Approximately 5.
*Anther shape.*—Tubular.
*Anther color.*—Near 15A.
*Pollen color.*—Near 15A.

OTHER CHARACTERISTICS

Disease resistance: Neither resistance nor susceptibility to diseases and pests have been observed in this cultivar.

Changes as flower ages: The disc becomes more open.

Seed production: Commercially, this plant is not used or observed in a stage wherein seeds would be produced. Therefore, seed production has not been observed.

What is claimed is:

1. A new and distinct variety of Chrysanthemum plant named 'MOZA CB 01' as herein illustrated and described.

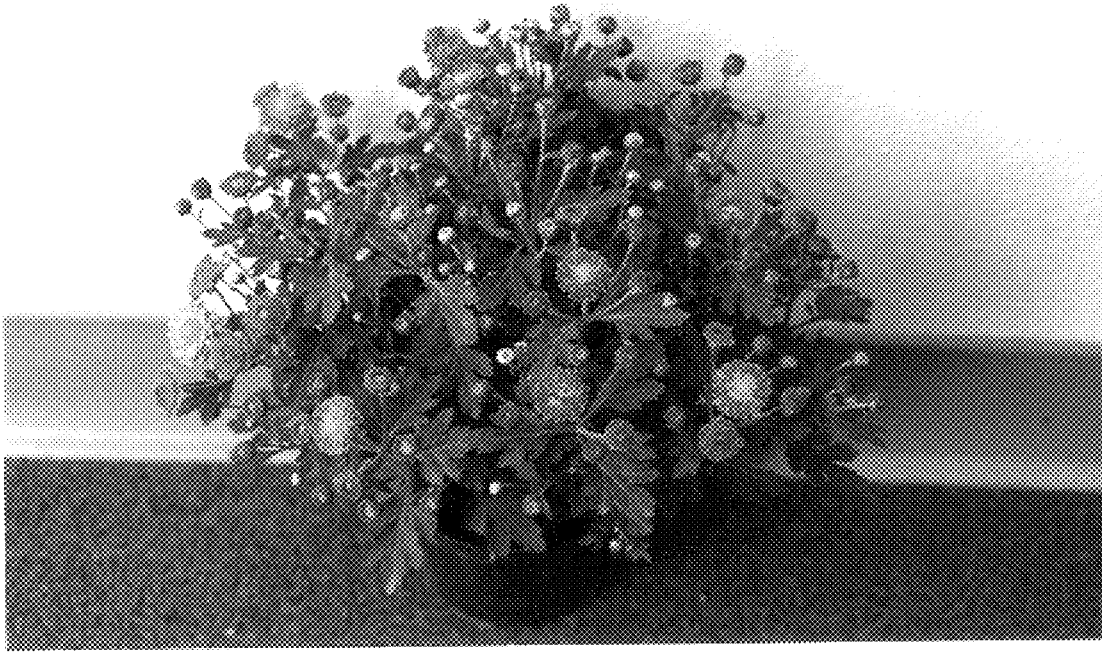

* * * * *